US00PP29871P3

(12) United States Plant Patent
Monge

(10) Patent No.: US PP29,871 P3
(45) Date of Patent: Nov. 20, 2018

(54) ***SANSEVIERIA* PLANT NAMED 'GREEN MERMAID'**

(50) Latin Name: *Sansevieria trifasciata*
Varietal Denomination: GREEN MERMAID

(71) Applicant: Luis Carlos Monge, Pavones (CR)

(72) Inventor: Luis Carlos Monge, Pavones (CR)

(73) Assignee: Fleurizon llc, Camarillo, CA (US)

( * ) Notice: Subject to any disclaimer, the term of this patent is extended or adjusted under 35 U.S.C. 154(b) by 0 days.

(21) Appl. No.: 15/330,681

(22) Filed: Oct. 25, 2016

(65) Prior Publication Data

US 2018/0116089 P1 Apr. 26, 2018

(51) Int. Cl.
*A01H 5/12* (2018.01)

(52) U.S. Cl.
USPC ..... Plt./382
CPC ..... *A01H 5/12* (2013.01)

(58) Field of Classification Search
USPC ..... Plt./373, 382
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Sansevieria* cultivar named 'GREEN MERMAID' is disclosed, characterized by foliage which is uniquely curved inward, and very straight upward. Foliage is distinctively strong and fibrous, dark green with lighter greyed-green marginal striations. The new variety is a *Sansevieria*, typically produced as an indoor ornamental plant.

3 Drawing Sheets

Latin name of the genus and species: *Sansevieria trifasciata.*

Variety denomination: 'GREEN MERMAID'.

BACKGROUND OF THE INVENTION

This application relates to a new cultivar of *Sansevieria trifasciata*. The new variety is the product of chance discovery. The inventor discovered the new variety as a whole plant, naturally occurring mutation from the parent plant *Sansevieria trifasciata* 'Black Gold', unpatented.

The new variety was first observed by the inventor, in December 2012 in a planting of the parent plant, at a commercial nursery in Costa Rica. After identifying the new variety as a potentially interesting selection, the inventor continued confidential testing and propagation of 'GREEN MERMAID', assessing stability of the unique characteristics of this variety.

Asexual reproduction of the new cultivar 'GREEN MERMAID' was first performed at a commercial nursery in Costa Rica by leaf cuttings of original plant in 2012. Through subsequent propagation, approximately 5 generations have been reproduced, which have shown that the unique features of this cultivar are stable and reproduced true to type.

SUMMARY OF THE INVENTION

The cultivar 'GREEN MERMAID' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'GREEN MERMAID'. These characteristics in combination distinguish 'GREEN MERMAID' as a new and distinct *Sansevieria* cultivar:

1. Foliage of the new variety is uniquely curved inward, and very straight upward. Most *Sansevieria* foliage curves outward or does not curve at all.
2. Foliage apex is uniquely broad acute and not sharp.
3. Unique marginal greyed-green striation and deep dark green main blade color.
4. Foliage is distinctively strong and hard, made up of exceptionally fibrous leaf tissue.

PARENT COMPARISON

Plants of the new cultivar 'GREEN MERMAID' are similar to the parent variety, in many horticultural characteristics. However the new variety, 'GREEN MERMAID' differs from parent in the following characteristics:

1. The parent variety does not have the same strong, fibrous leaf tissue.
2. Foliage of the new variety is very straight upright with an inward curve. Foliage of the parent variety is undulating, twisted and tends to curve outward.
3. The new variety has greyed-green marginal non-solid stripes, the parent variety has solid yellow marginal coloration.
4. Foliage apex of the new variety is less acute than that of the parent variety.
5. Plants of the new variety produce more suckers than plants of the parent variety.

COMMERCIAL COMPARISON

'GREEN MERMAID' can be compared with the unpatented commercial variety *Sanservieria*. 'Whitney', U.S. Plant Pat. No. 24,456. Plants of the new variety, 'GREEN MERMAID' differ from plants of 'Whitney' in the following characteristics:

1. Foliage of the new variety is narrower than foliage of 'Whitney', having an average width of 4.0 cm, compared to 8.5 cm.

2. Foliage of the new variety has greyed-green colored marginal striations, compared to the light green striations of the comparator.
3. Foliage of the new variety has a less acute apex than that of the comparator.
4. Plants of the new variety produce less leaves per plant than 'Whitney'.
5. Plants of the new variety are taller than plants of 'Whitney'
6. Plants of the new variety have narrow, ensiform leaves, compared to the wide lanceolate leaves of this comparator.
7. Foliage of the new variety is more flexible than foliage of 'Whitney'.

Plants of the new variety 'Green Mermaid' can also be compared to the commercial variety *Sansevieria* 'Black Robusta', unpatented. Plants of the new variety differ in the following:

1. Foliage of the new variety is narrower, averaging 4.0 cm, compared to foliage of 6 to 8 cm in width of the comparator.
2. Foliage of the new variety has greyed-green colored marginal striations, this comparator is heavily striated with light green and silver over the entire leaf.
3. Foliage of the new variety has a less acute apex than that of the comparator.
4. Plants of the new variety produce less leaves per plant than 'Black Robusta'.
5. Plants of the new variety are taller than plants of 'Black Robusta'.

BRIEF DESCRIPTION OF THE PHOTOGRAPHS

The accompanying photograph in FIG. 1 illustrates in full color a typical plant of 'GREEN MERMAID' at approximately 3 months grown in a commercial greenhouse in Costa Rica in a 6 inch pot.

Figure 1:
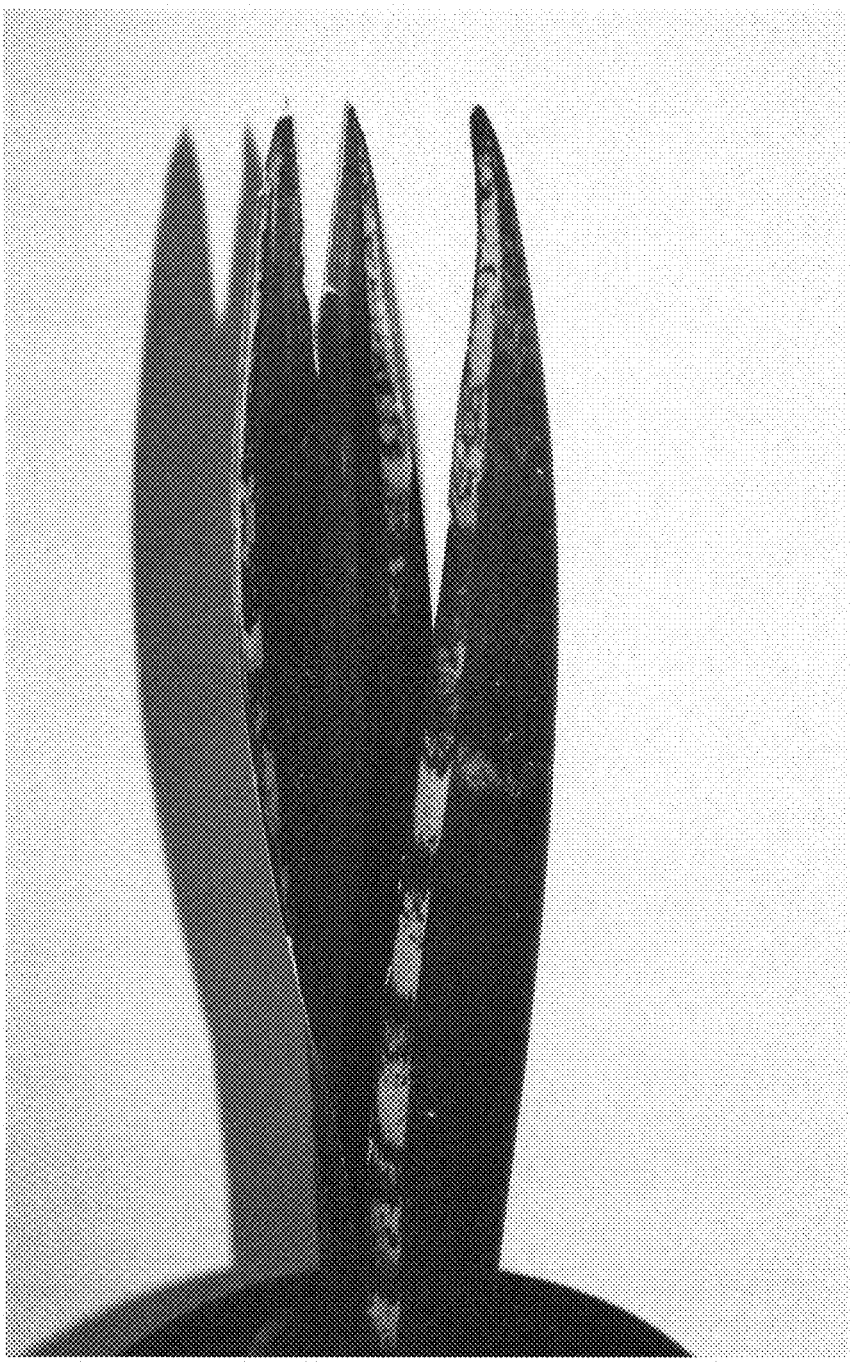
Figure 2:
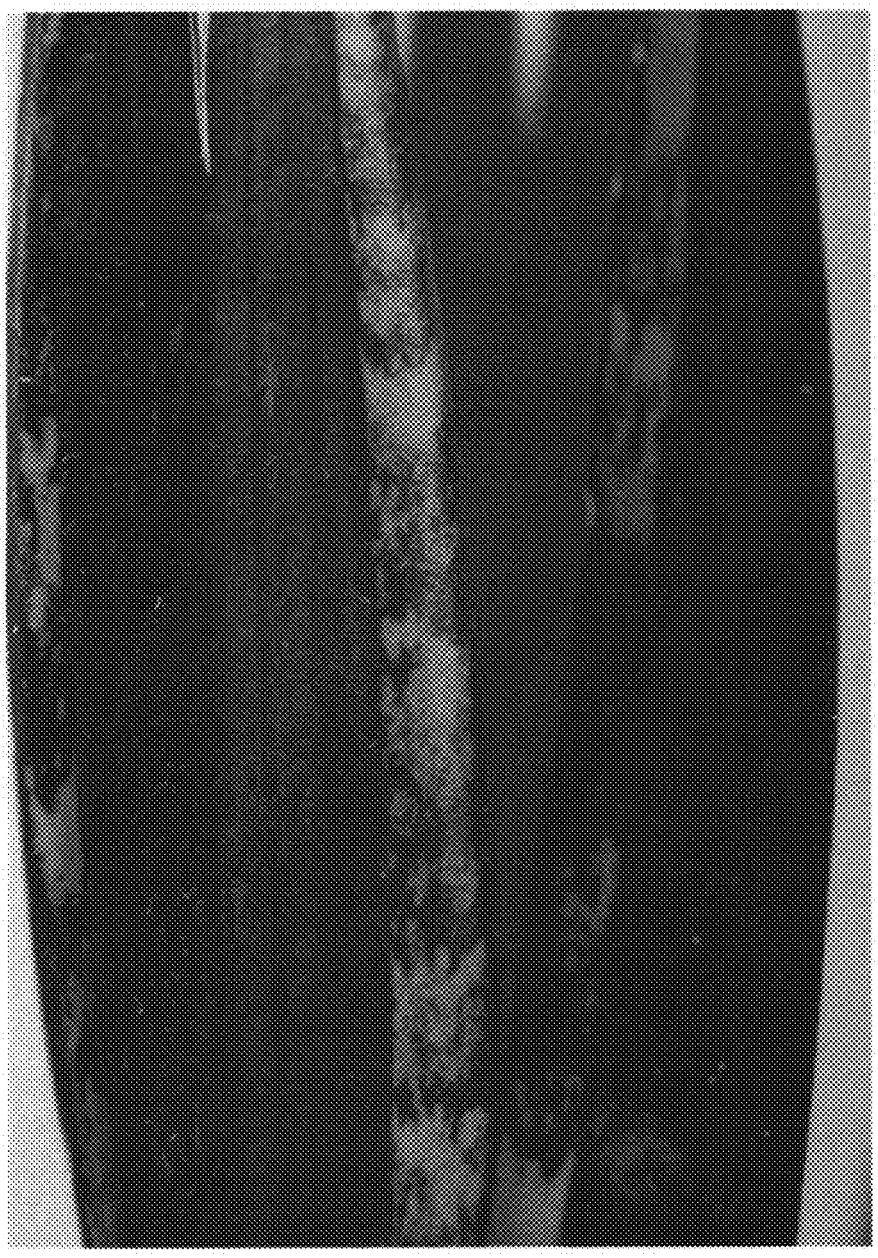
FIG. 2 illustrates a close up of the foliage.
Figure 3:
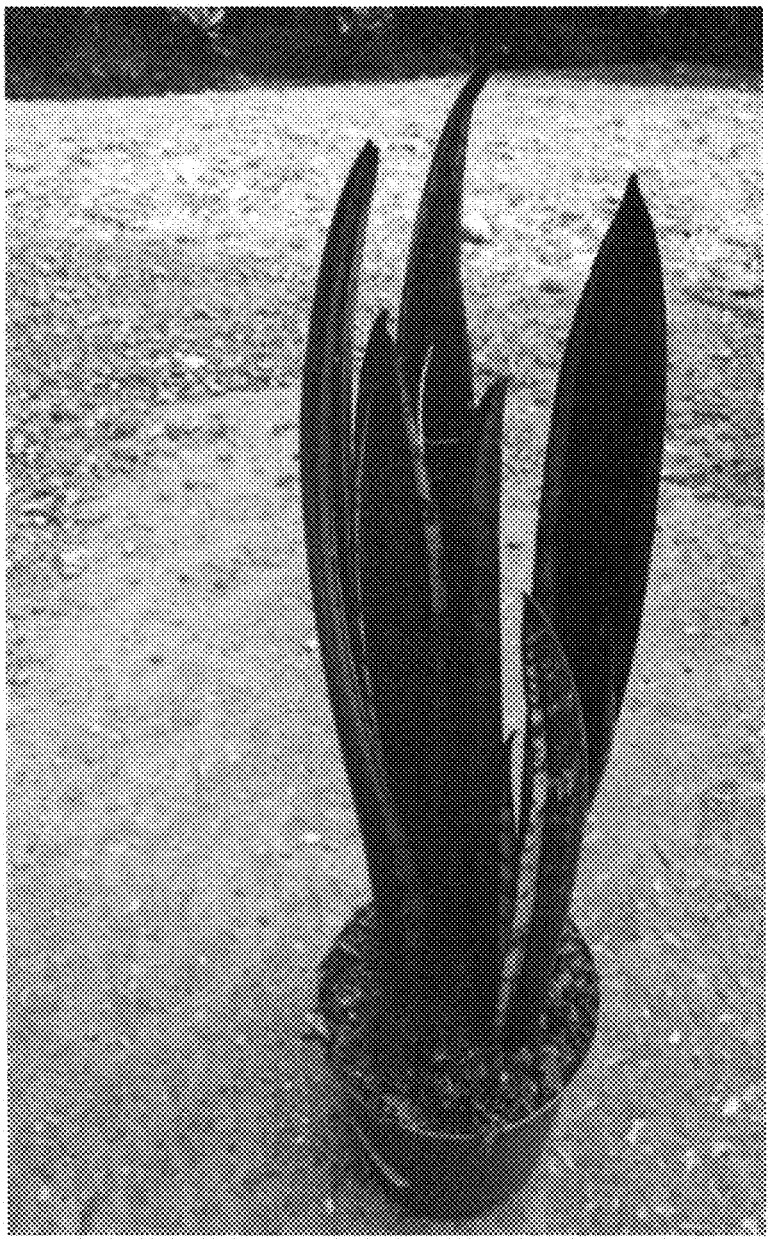
FIG. 3 illustrates somewhat older plants, 2 suckers in a pot of approximately 5 to 6 months grown in a 6 inch pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'GREEN MERMAID' plant is grown in Costa Rica. The plant is approximately 4 months old in a 6 inch pot. Temperatures ranged between 22° C. to 40° C. during the day and 15° C. to 30° C. at night. No chemical treatments were given to the plants. Measurements and numerical values represent averages of typical plant types.

Botanical classification: *Sansevieria trifasciata* 'GREEN MERMAID'.

PROPAGATION

Time to initiate rooting: About 2 to 3 months at approximately 17° C. to 40° C.

Root description: Moderately thick, slightly fleshy, slightly fibrous, moderately dense, moderately branched, colored greyed-orange, near RHS N170B.

PLANT

Growth habit: Monopodial, irregular rosulate.

Growth rate: Slightly faster than moderate.

Height: Approximately 35 to 40 cm at 3 to 4 months, approximately 45 to 60 cm at 5 to 6 months.

Plant spread: Approximately 9.0 cm.

Growth rate: Moderate. Approximately 5 to 6 months to a commercially finished plant.

Number of leaves per plant at 5 to 6 months: Average range: 2 to 3.

FOLIAGE

Leaf:

*Arrangement*.—Rosulate.

*Average length*.—Average 35 cm.

*Average width*.—Average 4.5 cm.

*Depth (thickness) of leaf blade*.—Approximately 2 mm slightly succulent.

*Shape of blade*.—Ensiform.

*Blade aspect*.—Strong inward fold.

*Growth aspect*.—Leaves grow completely upright.

*Apex*.—Acute, sometimes splitting into 2 acute aspices.

*Base*.—Decurrent.

*Margin*.—Entire.

*Texture of top surface*.—Glabrous, shallow, thick ribs.

*Texture of bottom surface*.—Glabrous.

*Appearance of top surface*.—Matte.

*Appearance of bottom surface*.—Matte.

*Color*.—Young foliage upper side: Darker than 139A, margins have a well-defined stripe of thick blotching Greyed-Green 193B and 193C. Young foliage under side: Darker than 139A, margins have a well-defined stripe of thick blotching Greyed-Green 193B and 193C. Mature foliage upper side: Darker than Yellow-Green 147A, tinged Greyed-Green N189A. Margins have a well-defined stripe of thick blotching Greyed-Green 193B and 193C. This distinct margin approximately 5 to 6 mm thick. Mature foliage under side: Darker than Yellow-Green 147A, tinged Greyed-Green N189A. Margins have a well-defined stripe of thick blotching Greyed-Green 193B and 193C. This distinct margin approximately 5 to 6 mm thick.

*Venation*.—Type: Parallel. Color: Upper side: Indistinguishable from leaf blade. Under side: Indistinguishable from leaf blade.

Sheath:

*Average length*.—Approximately 3.0 cm.

*Average width*.—Approximately 5 cm (clasping leaf base).

*Color*.—Near Yellow-Green 147C.

*Texture*.—Glabrous, moderately glossy.

*Other*.—Thin, papery sheath occurs under the soil.

Other distinguishing characteristics: Leaf is very strong and fibrous, resists breakage.

OTHER CHARACTERISTICS

Disease resistance: Neither resistance nor susceptibility to the normal diseases found in *Sansevieria* has been observed.

Fruit/seed production: No fruits/seeds detected to date.

What is claimed is:

1. new and distinct cultivar of *Sansevieria* plant named 'GREEN MERMAID' as herein illustrated and described.

* * * * *